United States Patent
Jasperse

(10) Patent No.: US 9,791,690 B2
(45) Date of Patent: *Oct. 17, 2017

(54) SHUTTER ASSEMBLY FOR A LUMINESCENCE-BASED SAMPLE ANALYZER

(71) Applicant: Siemens Healthcare Diagnostics Inc., Tarrytown, NY (US)

(72) Inventor: Jeffrey R. Jasperse, Newton, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/403,381

(22) PCT Filed: May 23, 2013

(86) PCT No.: PCT/US2013/042372
§ 371 (c)(1),
(2) Date: Nov. 24, 2014

(87) PCT Pub. No.: WO2013/181052
PCT Pub. Date: Dec. 5, 2013

(65) Prior Publication Data
US 2015/0097124 A1    Apr. 9, 2015

Related U.S. Application Data

(60) Provisional application No. 61/652,553, filed on May 29, 2012.

(51) Int. Cl.
*G02B 26/04* (2006.01)
*G01N 21/64* (2006.01)
(Continued)

(52) U.S. Cl.
CPC ............. *G02B 26/04* (2013.01); *G01N 21/64* (2013.01); *G01N 21/645* (2013.01); *G01N 33/50* (2013.01);
(Continued)

(58) Field of Classification Search
CPC ................................ G02B 26/04; G01N 21/64
See application file for complete search history.

(56) References Cited

U.S. PATENT DOCUMENTS 2,922,349 A    1/1960    Rochwite
3,903,528 A    9/1975    Kee
(Continued)

FOREIGN PATENT DOCUMENTS

CN    1664689 A    9/2005
CN    101266386 A    9/2008
(Continued)

OTHER PUBLICATIONS

International Search Report and Written Opinion of International Application No. PCT/US2013/042372 dated Oct. 2, 2013.
(Continued)

*Primary Examiner* — Jason McCormack
*Assistant Examiner* — Sean Luck
(74) *Attorney, Agent, or Firm* — Kyle D. Petaja

(57) ABSTRACT

A shutter assembly includes a first shutter blade having a first toothed arm extending therefrom and a first light transmitting aperture therein, and a second shutter blade positioned adjacent and parallel to the first shutter blade. The second shutter blade has a second toothed arm extending therefrom and a second light transmitting aperture therein. The first and second shutter blades are supported to allow parallel linear motion. A motor gear is disposed between, and meshed with, the first and second toothed arms such that rotation of the gear causes the first and second shutter blades (Continued)

to move linearly in opposite directions between an open position in which the first and second light transmitting apertures are in an overlapping relationship with respect to one another, and a closed position in which the first and second light transmitting apertures are in a non-overlapping relationship with respect to one another.

28 Claims, 10 Drawing Sheets

(51) Int. Cl.
*H01J 43/00* (2006.01)
*G01N 33/50* (2006.01)
*G03B 9/14* (2006.01)
*G03B 11/04* (2006.01)

(52) U.S. Cl.
CPC ...... *H01J 43/00* (2013.01); *G01N 2201/0221* (2013.01); *G01N 2201/068* (2013.01); *G01N 2201/0648* (2013.01); *G03B 9/14* (2013.01); *G03B 11/043* (2013.01)

(56) References Cited

U.S. PATENT DOCUMENTS

| | | | |
|---|---|---|---|
| 3,918,077 A | 11/1975 | Burton et al. | |
| 3,928,859 A | 12/1975 | Peterson | |
| 4,007,469 A | 2/1977 | Land et al. | |
| 4,112,450 A | 9/1978 | Kondo | |
| 4,176,929 A | 12/1979 | Ito et al. | |
| 4,827,348 A | 5/1989 | Ernest et al. | |
| 4,978,991 A | 12/1990 | Farrington | |
| 5,408,363 A | 4/1995 | Kano | |
| 5,709,994 A | 1/1998 | Pease et al. | |
| 5,833,924 A | 11/1998 | McClintock et al. | |
| 6,139,153 A | 10/2000 | Alscher et al. | |
| 6,313,471 B1 | 11/2001 | Giebeler et al. | |
| 6,466,353 B2 | 10/2002 | Tuchman | |
| 6,495,373 B1 | 12/2002 | Mauchan | |
| 6,850,351 B1* | 2/2005 | Djachiachvili | ........ G02B 26/04 352/215 |
| 7,402,281 B2 | 7/2008 | Huynh-Ba et al. | |
| 2007/0177049 A1* | 8/2007 | Kreysar | .................... G01J 1/04 348/368 |
| 2008/0129736 A1 | 6/2008 | Sun et al. | |
| 2010/0024526 A1 | 2/2010 | Colvin, Jr. et al. | |
| 2010/0276605 A1 | 11/2010 | Olsen et al. | |
| 2011/0007312 A1 | 1/2011 | Bushaw et al. | |
| 2012/0231493 A1 | 9/2012 | Noda et al. | |

FOREIGN PATENT DOCUMENTS

| | | |
|---|---|---|
| EP | 0325410 A1 | 7/1989 |
| GB | 456617 A | 11/1936 |
| GB | 1474038 A | 5/1977 |
| JP | S5011432 A | 2/1975 |
| JP | S5158329 A | 5/1976 |
| JP | S52117124 A | 10/1977 |
| JP | S54008523 A | 1/1979 |
| JP | S60249123 A | 12/1985 |
| JP | H01257927 A | 10/1989 |
| JP | H05-90457 U | 12/1993 |
| JP | H0643090 A | 2/1994 |
| JP | 2004348051 A | 12/2004 |
| JP | 2007156230 A | 6/2007 |
| WO | 2009111834 A1 | 9/2009 |

OTHER PUBLICATIONS

Supplemental Partial European Search Report of European Application No. 13798044 dated Apr. 1, 2016.

* cited by examiner

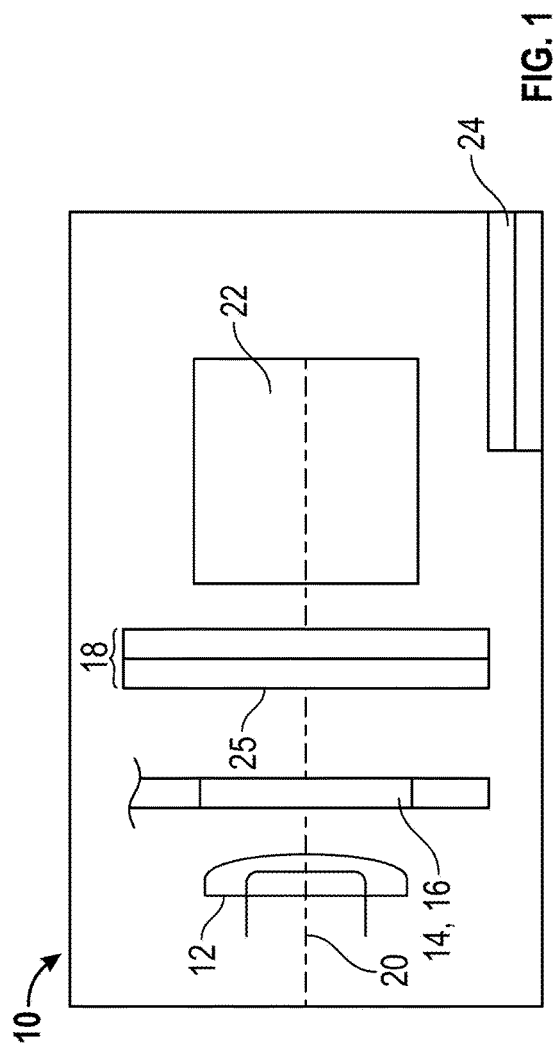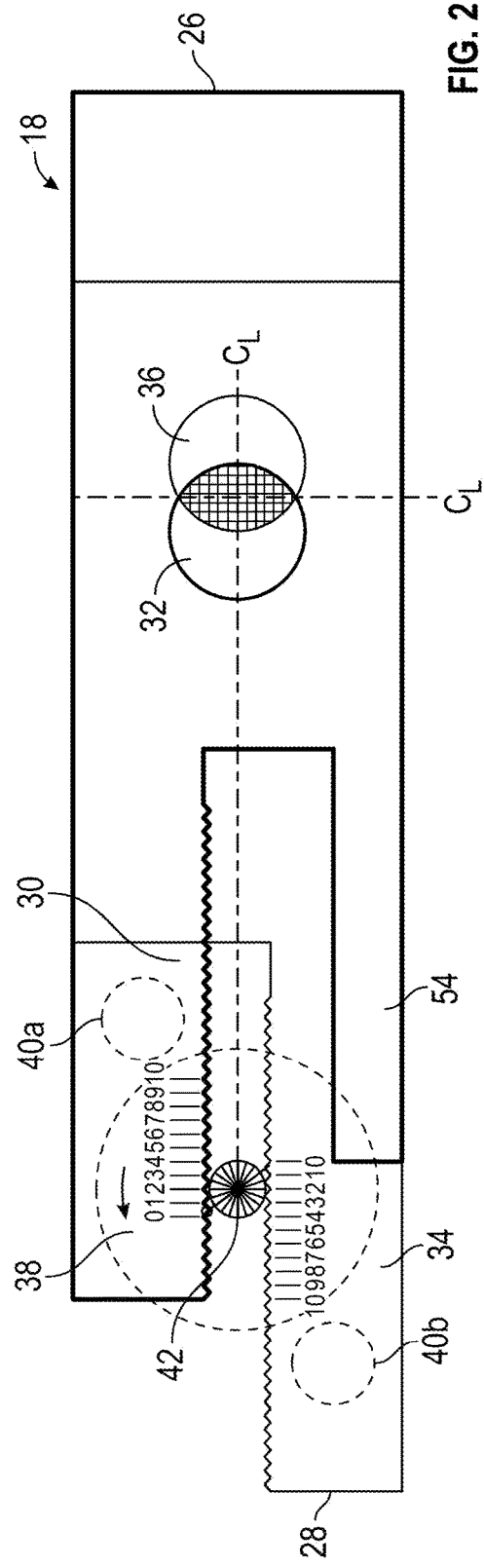

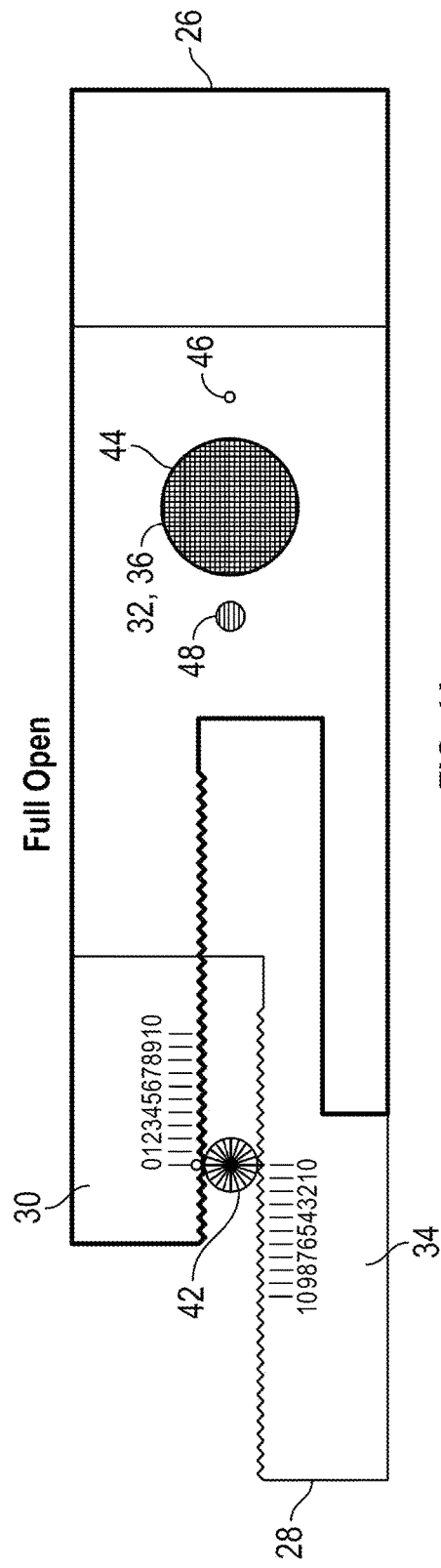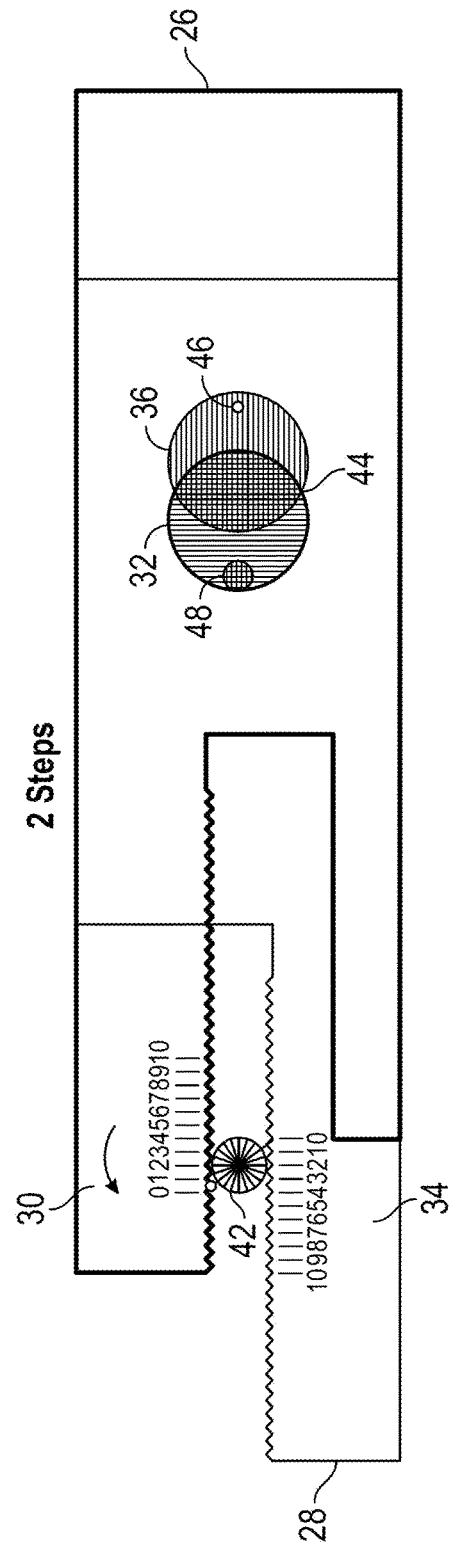

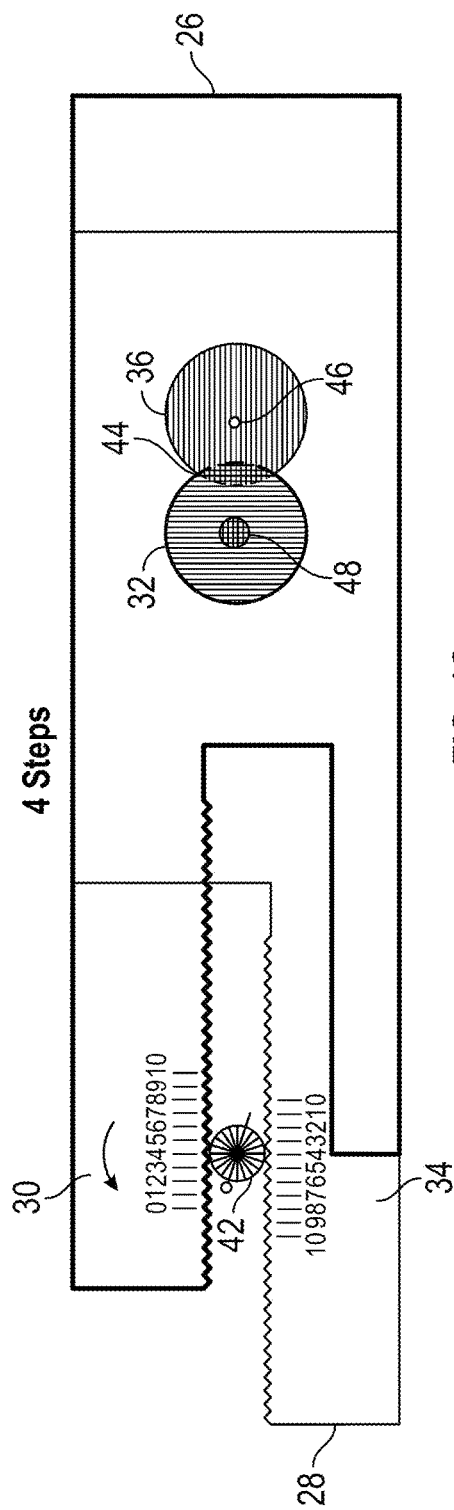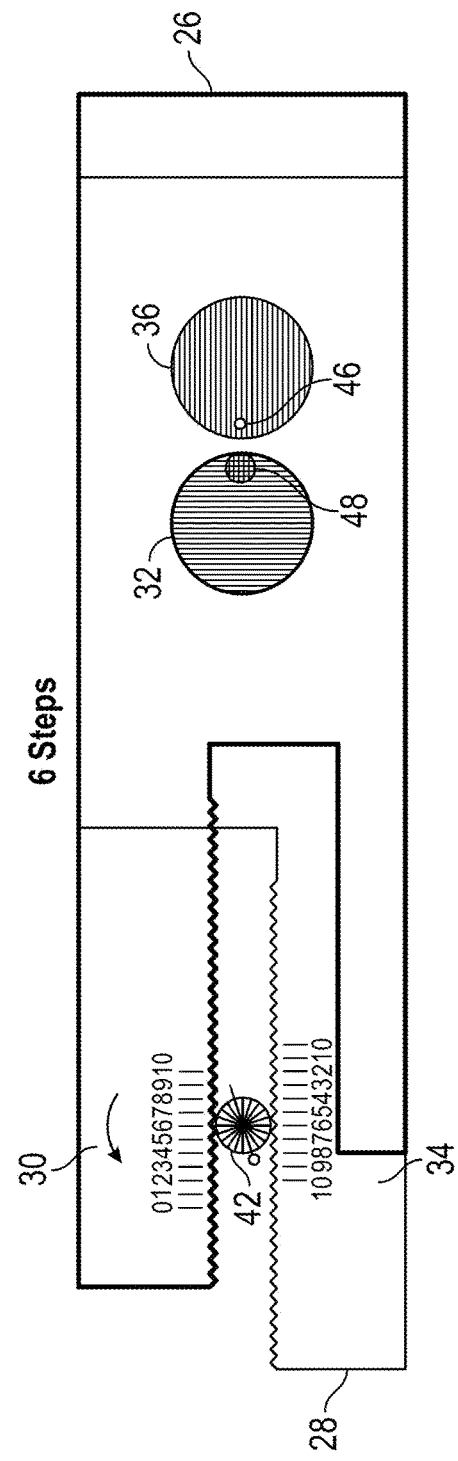

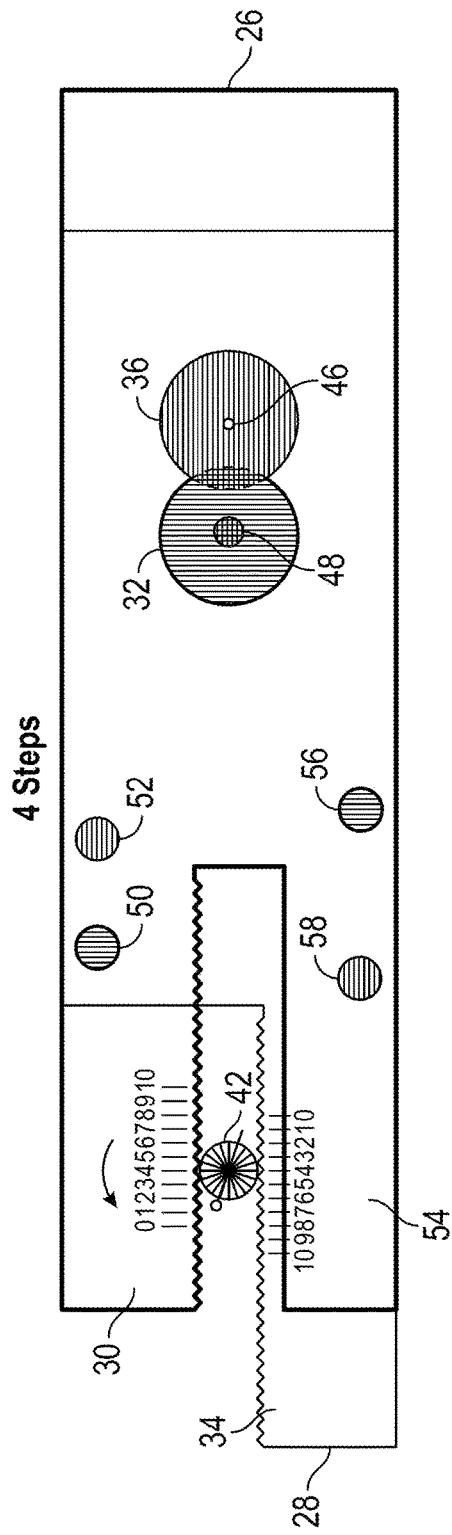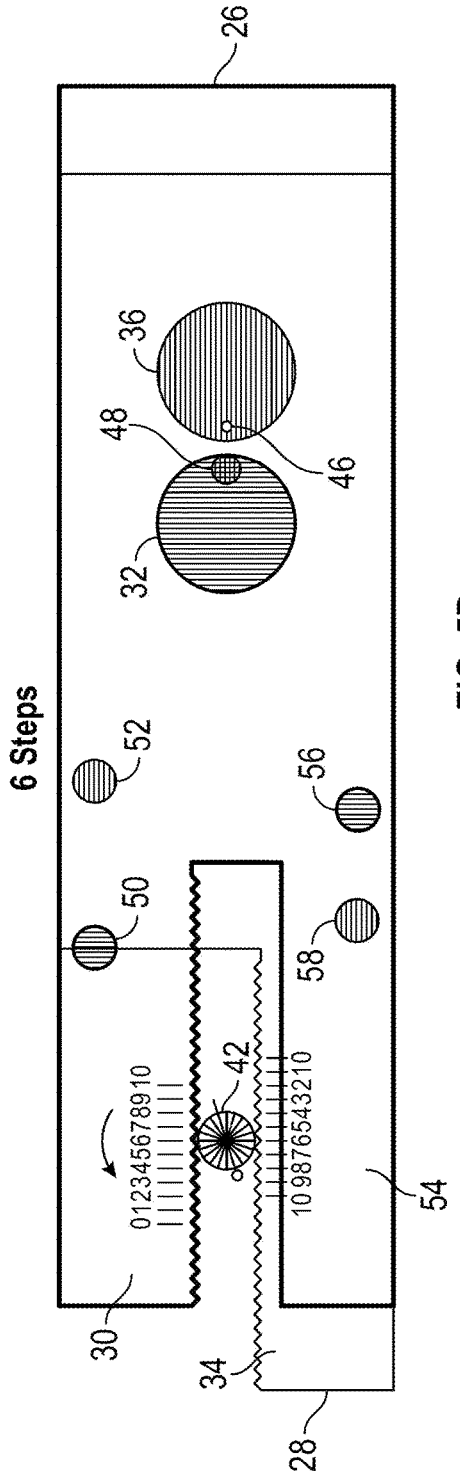

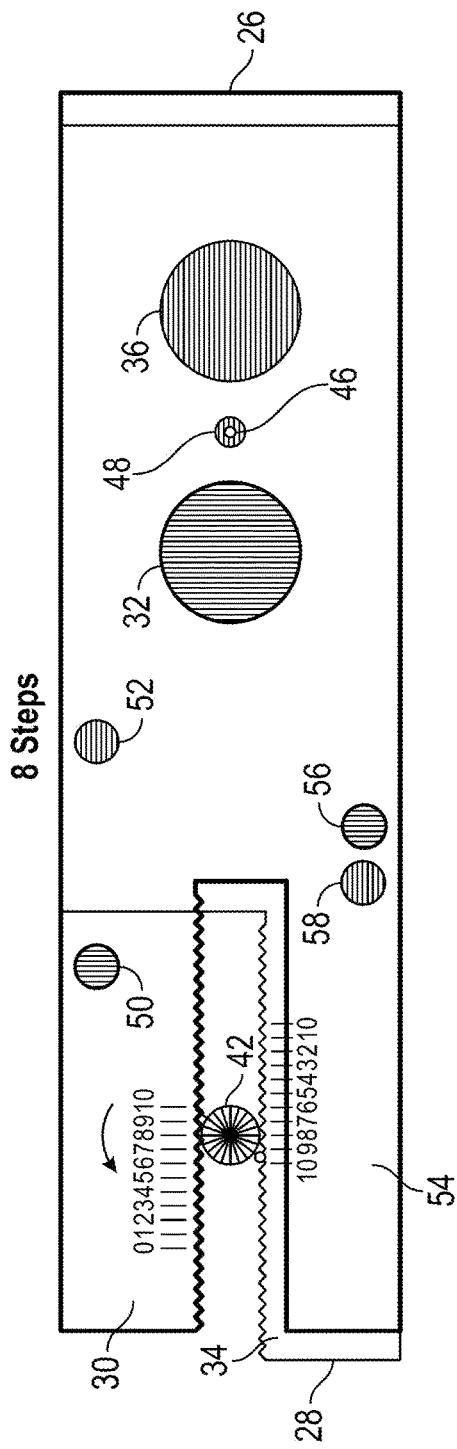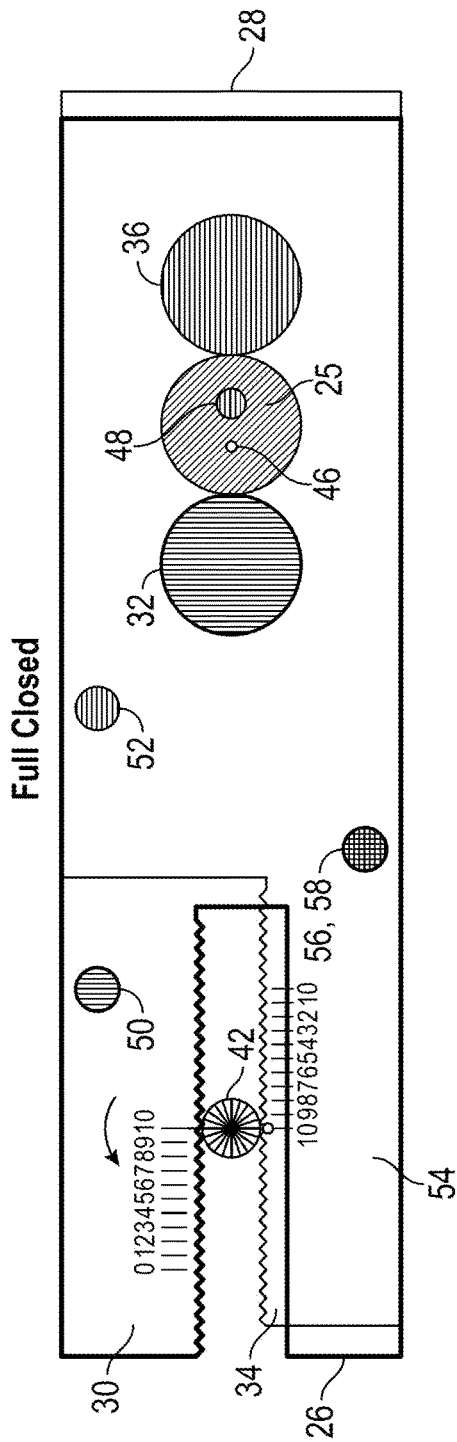
FIG. 5E
FIG. 5F

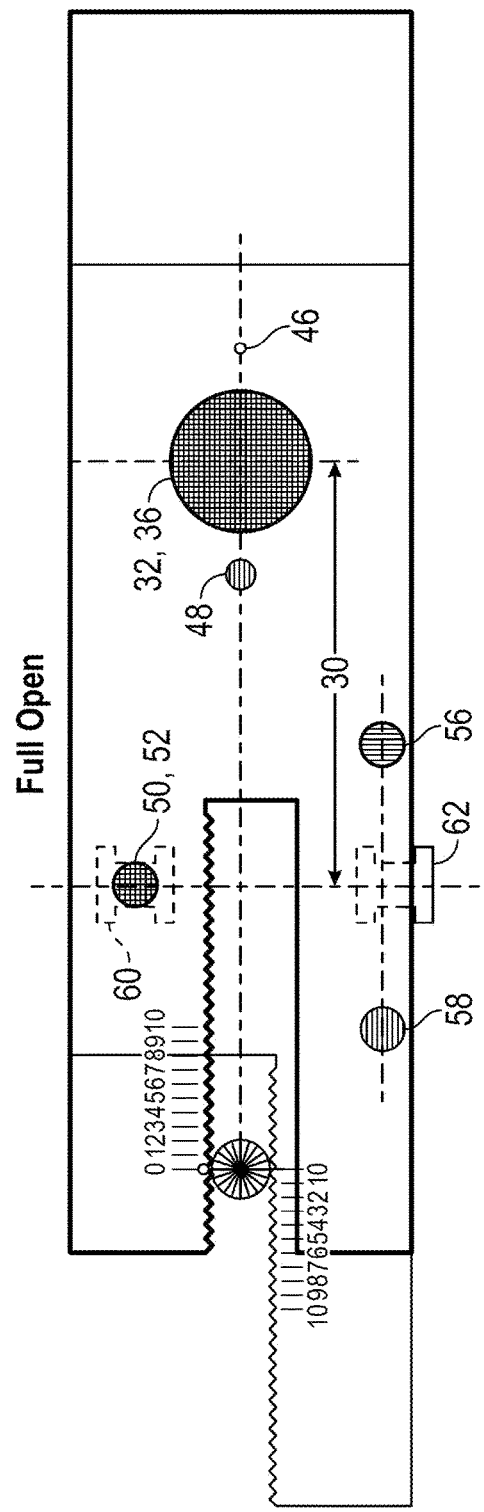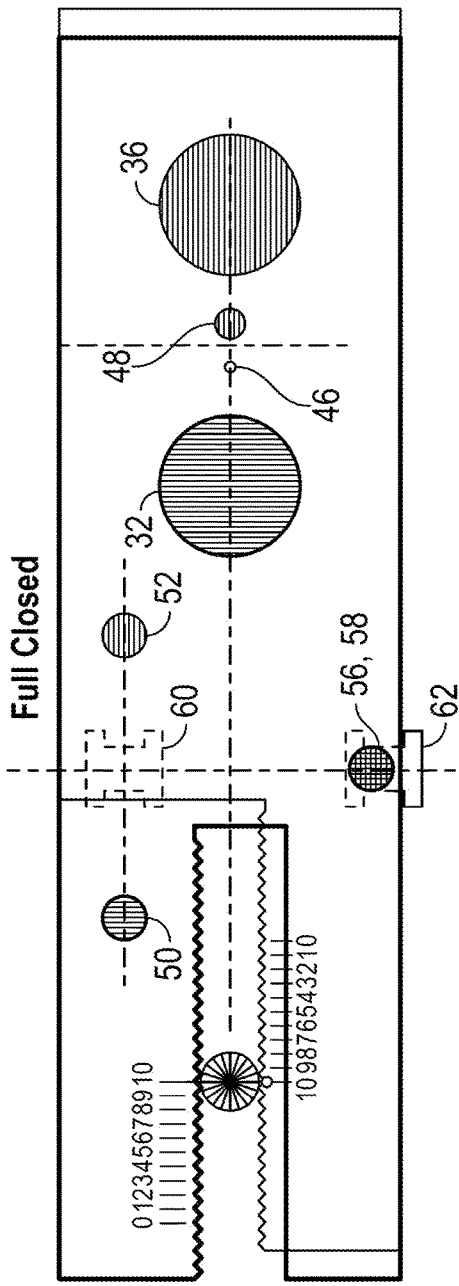

SHUTTER ASSEMBLY FOR A LUMINESCENCE-BASED SAMPLE ANALYZER

CROSS-REFERENCE TO RELATED APPLICATIONS

The entirety of U.S. Provisional Application Ser. No. 61/652,553, filed on May 29, 2012, is hereby expressly incorporated herein by reference.

STATEMENT REGARDING FEDERALLY SPONSORED RESEARCH OR DEVELOPMENT

Not applicable.

BACKGROUND OF THE INVENTIVE CONCEPTS

1. Field of the Inventive Concepts

The inventive concepts disclosed and claimed herein relate generally to shutters, and more particularly, but not by way of limitation, to a shutter assembly for protecting a sensitive light detector such as a photomultiplier tube against harmful exposure to light.

2. Brief Description of Related Art

Analytical instrumentation utilizing luminescence detection is heavily utilized in the pharmaceutical and medical industries. Analytical measurements are often performed using a beam of catalyzing radiation to interact with a specific sample-reagent combination. The resulting photon emission, often very weak, is then detected and measured with a sensitive detector, converted to an electrical signal, and further correlated to provide the actual analytical result.

For example, U.S. Pat. No. 5,709,994 discloses a highly sensitive method of assaying known as a Luminescent Oxygen Channeling Immunoassay (LOCI). The method uses a photosensitizer that generates singlet oxygen upon irradiation, and a chemiluminescent compound that is activated by the singlet oxygen. The photosensitizer and chemiluminescent compound are irradiated with light of a certain wavelength, after which the resulting light emitted by chemiluminescent compound is measured and correlated to provide the assay.

The instrumentation utilized for luminescence-based assays is often physically large due, in part, to the intricate and sensitive optics used. The analyses often involve exposure of the sample to a high intensity light near the field of view of a sensitive detector such as a photomultiplier tube. To protect the sensitive detector, it is common to widely separate the detector from the high intensity light source and to provide path barriers and shutters between the two.

Size is not a major concern in large laboratories facilitating high-throughput screening; however, it would be useful to have a lighter, portable unit or handheld device capable of producing accurate luminescence-based analyses for non-laboratory settings, such as, medical clinics, physicians offices and homes. Compact designs that reduce the optical path can also increase the risk of harmful exposure of the sensitive detector to the high intensity light source.

In view of the foregoing, there is an increasing need for a shutter design that is compact, energy-efficient, and suitable for protecting sensitive detectors in a portable luminescence-based sample analyzer. It is to such a shutter design that the presently disclosed and claimed inventive concept(s) is directed.

SUMMARY OF THE INVENTIVE CONCEPTS

The inventive concepts disclosed and claimed herein generally relate to a shutter assembly for interrupting light transmission. The shutter assembly includes a first shutter blade having a first toothed arm extending therefrom and a first light transmitting aperture therein, and a second shutter blade positioned adjacent and parallel to the first shutter blade. The second shutter blade has a second toothed arm extending therefrom and a second light transmitting aperture therein. The first and second shutter blades are supported to allow parallel linear motion. A motor gear is disposed between, and meshed with, the first and second toothed arms such that rotation of the gear causes the first and second shutter blades to move linearly in opposite directions between an open position in which the first and second light transmitting apertures are in an overlapping relationship with respect to one another, and a closed position in which the first and second light transmitting apertures are in a non-overlapping relationship with respect to one another.

BRIEF DESCRIPTION OF THE DRAWINGS

Like reference numerals in the figures represent and refer to the same or similar element or function. Implementations of the disclosure may be better understood when consideration is given to the following detailed description thereof. Such description makes reference to the annexed pictorial illustrations, schematics, graphs, and drawings. The figures are not necessarily to scale and certain features and certain views of the figures may be shown exaggerated, to scale or in schematic in the interest of clarity and conciseness. In the drawings:

FIG. 1 is a schematic representation of an embodiment of a sample analyzer constructed in accordance with the inventive concepts disclosed herein.

FIG. 2 is a schematic representation of an embodiment of a shutter assembly constructed in accordance with the inventive concepts disclosed herein.

FIG. 4A-FIG. 4F provide a schematic representation of a shutter assembly embodiment operating in accordance with the inventive concepts disclosed herein.

FIG. 5A-FIG. 5F provide a schematic representation of another shutter assembly embodiment operating in accordance with the inventive concepts disclosed herein.

FIG. 6A-FIG. 6C provide a schematic representation of yet another shutter assembly embodiment showing use and placement of reference aperture sensors.

DETAILED DESCRIPTION OF EXEMPLARY EMBODIMENTS

Figure 3:
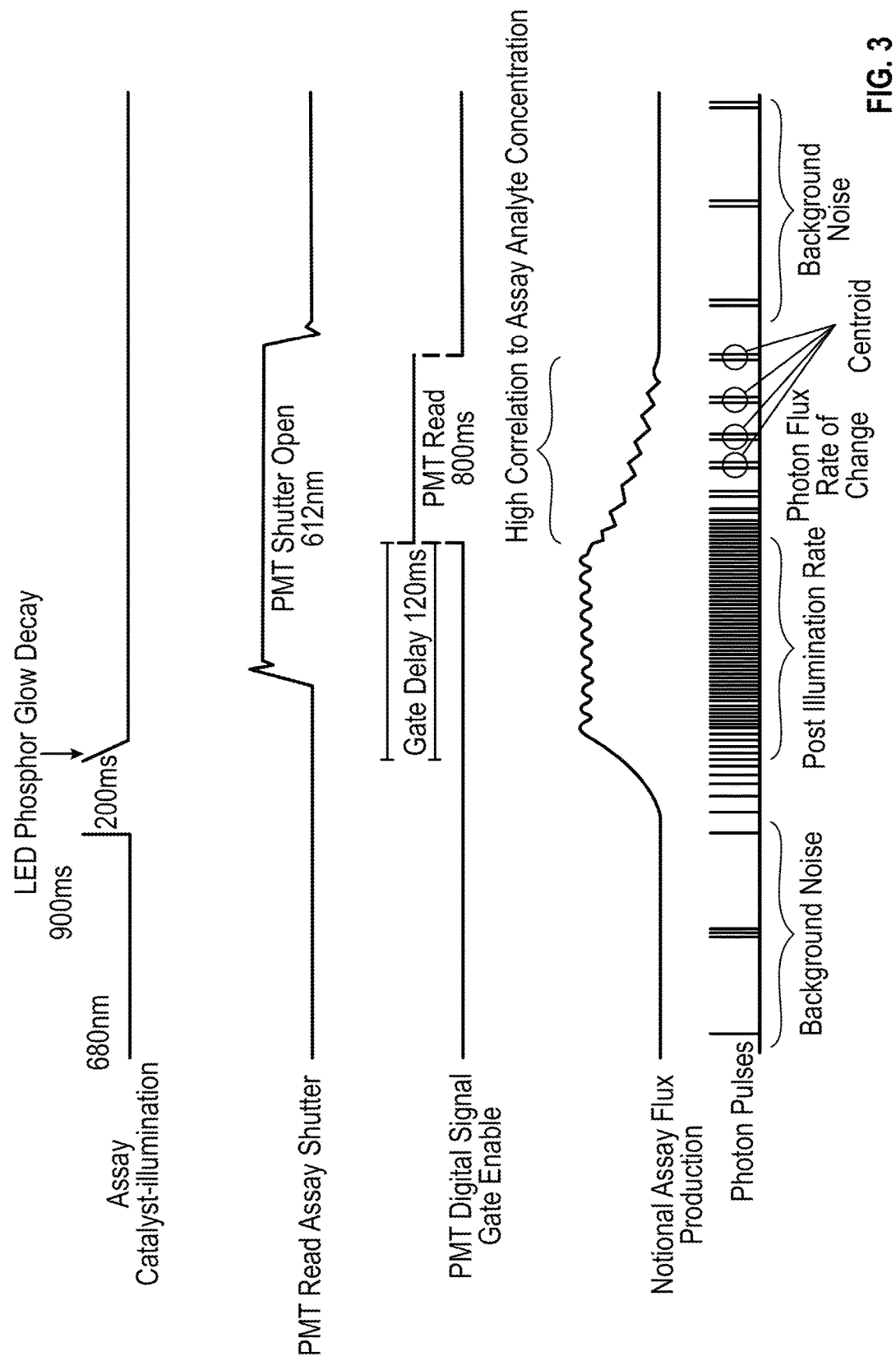
FIG. 3 is a timing diagram for an embodiment of a sample analyzer operation in accordance with the inventive concepts disclosed herein.

Before explaining at least one embodiment of the inventive concept disclosed herein in detail, it is to be understood that the inventive concept is not limited in its application to the details of construction, experiments, exemplary data, and/or the arrangement of the components set forth in the following description, or illustrated in the drawings. The presently disclosed and claimed inventive concept is capable of other embodiments or of being practiced or carried out in various ways. Also, it is to be understood that the phraseology and terminology employed herein is for purpose of description only and should not be regarded as limiting in any way.

In the following detailed description of embodiments of the inventive concept, numerous specific details are set forth in order to provide a more thorough understanding of the inventive concept. However, it will be apparent to one of ordinary skill in the art that the inventive concept within the disclosure may be practiced without these specific details. In other instances, well-known features have not been described in detail to avoid unnecessarily complicating the instant disclosure.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or at least one and the singular also includes the plural unless it is obvious that it is meant otherwise.

References to the Luminescent Oxygen Channeling Immunoassay (LOCI) methods and optical systems are for example only, and the inventive concepts can be used with any sample analysis procedure utilizing optical detection to measure luminescence, fluorescence, absorbance, and turbidity. Reference to a "sample" or "assay sample" refers to the sample to be analyzed and includes reagents added according to the analysis procedure, those reagents added either before or after insertion into the assay sample vessel.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Referring now to the drawings, and more particularly to FIG. 1, shown therein is an exemplary embodiment of a sample analyzer 10 constructed in accordance with the inventive concepts disclosed and claimed herein. The sample analyzer 10 comprises an illuminator 12 for illuminating an assay sample 14 positioned and contained within a sample reservoir 16 to cause luminescence. A shutter assembly 18 is positioned along an optical axis 20 to protect the sensitive optics of detector 22 from high intensity illumination from the illuminator 12. The detector 22 measures the luminescence or light emitted from assay sample 14 as a result of the illumination.

The illuminator 12 can be multi-wavelength, optionally filtered to cut off undesired wavelengths, or can be a laser providing monochromatic light. Light intensity and time of irradiation may vary widely. In one embodiment, light emitting diodes (LEDs) are used. In another embodiment, the illuminator 12 comprises multiple LEDs arranged in a ring.

The detector 22 can be any known or yet to be developed photo-detector having a sensitivity required by the particular assay. For example, vacuum photodetectors such as photomultiplier tubes (PMTs) are typically very sensitive compared to solid state photodetectors such as silicon photodiodes. Photodetectors and their use are well known to those skilled in the art.

Optical axis 20 is defined herein by a line directed from the illuminator 12 to the detector 22. In some embodiments, and as shown in FIG. 1, optical axis 20 also coincides with a line directed from the positioned sample reservoir 16 to the detector 22. Such alignment of the illuminator 12 with both the sample reservoir 16 and the detector 22 provides a shortened optical path for both illumination and measuring modes. This in turn allows a more compact design and reduced power requirements compared to existing laboratory luminescence-based sample analyzers. For example, in one embodiment, the detector 22 is positioned about 10 mm or less from the assay sample 14. In another embodiment, the detector 22 is positioned about 5 mm or less from the assay sample 14. This is significantly more compact than present bench scale sample analyzers wherein the distance between the detector and the assay sample is on the order of 80 mm or more. Also, in one embodiment, the detector 22 is positioned about 5 mm from the illuminator 12. This is a significant achievement, particularly in embodiments utilizing a photomultiplier tube to measure extraordinarily low light signals of interest on the order of 50 photons per second output. Such compaction provides embodiments wherein the sample analyzer 10 is portable and/or hand-held and the power supply 24 is one or more batteries.

The shutter assembly 18 operates to remain closed during the illumination interval, thereby blocking light transmission from the illuminator 12 to the detector 22 and protecting the detector 22 from over exposure. During the illumination interval, light shines into the assay sample reservoir 16, activating the assay sample 14 to start the reaction and photon emission. After the illumination interval, the assay sample 14 begins to respond by emitting photons and during this measuring mode, the shutter assembly 18 remains open to allow light emitted by the assay sample to enter and be measured by detector 22. This unique design enables the use of rigid, dense blade material, such as metal alloys, achieving the highest degree of optical density performance possible while providing high speed shutter opening and closing, a critical need in high intensity illumination applications that use a high sensitivity photon detector.

In one embodiment, a surface 25 of the shutter assembly 18 facing the illuminator 12 is reflective, such that light from the illuminator 12 passing through the assay sample 14 is reflected by the surface 25 back toward the assay sample 14. This increases the illumination penetrating the assay sample 14 and thereby improves the assay sample activation. A nonlimiting example of a suitable reflective surface 25 is polished stainless steel.

As shown in FIG. 2, the shutter assembly 18 comprises a first shutter blade 26 and a second shutter blade 28. First shutter blade 26 is planar in shape with a first toothed arm 30 extending therefrom and a first light transmitting aperture 32 therein. Similarly, the second shutter blade 28 is planar in shape with a second toothed arm 34 extending therefrom and a second light transmitting aperture 36 therein. The second shutter blade 28 is positioned adjacent and parallel to the first shutter blade 26, and both shutter blades 26 and 28 are slideably supported on shutter assembly 18 to allow parallel linear motion.

First and second shutter blades 26 and 28 are typically shaped as thin metal blades with dimensions determined, in large part, by the sizes of the sample reservoir 16 and detector 22. Suitable construction can include any rigid material that is impervious to light. A variety of suitable metal alloys and polymers are known to those skilled in the art and are readily available commercially.

In one prototype, the first and second shutter blades 26 and 28 were constructed of 0.127 mm thick 304 stainless steel. This material is readily available and provided a high degree of light blocking. The blades were treated with a black oxide coating to prevent photon tunneling and reflections. The friction caused between the blades was low, thereby providing a low torque requirement and allowing high speed operation.

The reflective surface 25 can be present on at least a portion of the first or second shutter blades 26 and 28, wherein that portion represents the shutter blade surface exposed to illumination penetrating through the assay sample 14 during the illumination interval. It has been found that when first and second shutter blades 26 and 28 are constructed of stainless steel, polishing a portion of the stainless steel to produce the reflective surface 25 is sufficient to increase the illumination penetrating the assay sample 14 and to improve the assay sample activation. First shutter blade 26 can include a lower arm 54 which does not require teeth as do first and second toothed arms 30 and 34.

The shutter assembly 18 is operated by an actuator mechanism to cause the first and second shutter blades 26 and 28, respectively, to move linearly in opposite directions between an open position in which the first and second light transmitting apertures 32 and 36 are in an overlapping relationship with respect to one another, and a closed position in which the first and second light transmitting apertures 32 and 36 are in a non-overlapping relationship with respect to one another. Non-limiting examples of a suitable shutter actuator mechanism include a motor and solenoid with linkage to the shutter working against a spring, and a stepper motor.

A spring (not shown) or the like may be used to urge the first and second shutter blades 26 and 28 into a closed position to protect the detector 22. Shutters, such as those used in cameras and laboratory instrumentation utilizing optical detection, such as luminescence, fluorescence, absorbance measurements, are commonly controlled using a solenoid working against a spring. The solenoid requires continued power input to work against the spring or the like to maintain the shutter in an open position. The analytical instruments requiring shutters are usually powered by AC current, and the solenoid power requirements are not a major concern. Battery power drain is not significant with camera shutters because the shutter typically does not remain open for long periods. However, because of the relatively long time the shutter must remain open in luminescence-based sample analyzers, the power required for operation of a solenoid-controlled shutter in a battery-operated luminescence-based sample analyzer is significant.

In one embodiment, a motor 38, attached to the shutter assembly 18 by, for example, mountings 40a and 40b, provides a gear 42 which is disposed between, and meshed with, the first and second toothed arms 30 and 34, respectively. Rotation of gear 42 causes the first and second shutter blades 26 and 28, respectively, to move linearly in opposite directions between an open position in which the first and second light transmitting apertures 32 and 36 are in an overlapping relationship with respect to one another, and a closed position in which the first and second light transmitting apertures 32 and 36 are in a non-overlapping relationship with respect to one another.

In one embodiment, motor 38 is a stepper motor. A stepper motor is a brushless, electric motor having a number of "toothed" electromagnets arranged around a central gear-shaped bar of iron, each electromagnet providing a "step." A full rotation is thus divided into a number of individual steps, and the motor's position can be precisely controlled without requiring a feedback mechanism. As the speed of the stepper motor increases, torque decreases. The maximum torque occurs when the motor is stationary, and this "holding torque" determines the ability of the motor to maintain a desired position under external load. Thus, stepper motor 38 advantageously provides a holding torque which can be used to maintain the shutter blades in a precisely controlled position, whether closed, full open, or any position between. Because the stepper motor 38 requires no power to maintain a shutter position, it reduces the power requirements of a portable luminescence-based analyzer making such battery powered devices practical.

Additionally, the time taken for stepper motor 38 to open first and second shutter blades 26 and 28, respectively, is fast, due in part because the mass of the shutter blades and resulting inertia is small, and because the stepper motor 38 can be run at its highest velocity, sometimes called "high speed slewing." Thus, the shutter assembly 18 utilizing stepper motor 38 can be used to control the exposure time of the detector 22 in addition to protecting the detector 22 from light from the illuminator 12.

In a typical LOCI assay method such as for Troponin I, a patient blood plasma sample is mixed with chemi-bead and biotinylated antibody reagents and incubated at 37° C. for a specified time. This sample reagent mixture is then added to the sensi-bead reagent and incubated at 37° C. for a specified time. This mixture is diluted with assay diluent resulting in a assay sample which is illuminated with 680 nm light. This causes singlet oxygen release and shortly afterward emission of 612 nm photons which are measured by an optical detection system. FIG. 3 is an example timing diagram depicting a LOCI Troponin I assay. Process timing is shown for the illumination step, operation of photomultiplier shutter assembly and signal gates, and the production and analysis of photons emitted from the catalyst in the assay sample. FIG. 3 timing sequence detail: First the assay sample is illuminated; Second the shutter is opened to expose the detector optics to the assay sample; Third the detector is logically enabled to collect photon emission; Fourth the detector collecting photon emission is logically disabled; Fifth the shutter is closed to occlude and protect the detector. The Notional Assay Flux Production waveform represents the signal of interest, the output of the assay sample is proportional to the analyte concentration.

Figure 4E:
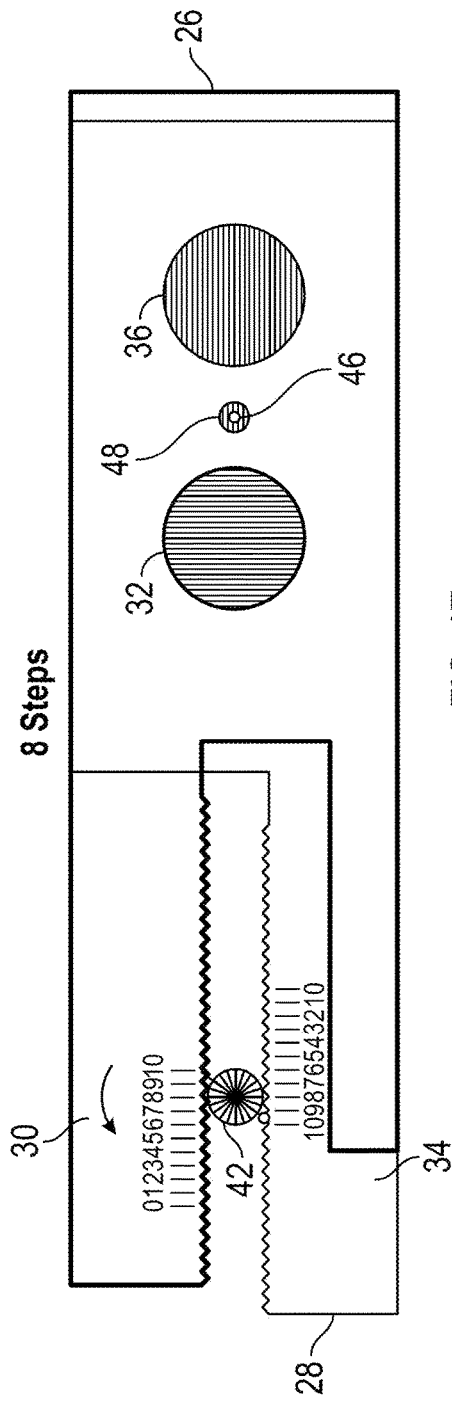

Referring now to FIG. 4A, the first and second shutter blades 26 and 28 are noted at stepper motor 38 position "0" coinciding with the first and second light transmitting apertures 32 and 36, respectively, being fully aligned thereby providing a full effective aperture 44 and noted as "FULL OPEN." FIG. 4B through FIG. 4F show an example of the relative positions of the shutter blades and apertures as stepper motor gear 42 progresses in 2-step intervals. After 6 steps, FIG. 4D shows no overlap of the first and second light transmitting apertures 32 and 36, respectively, and therefore no effective aperture 44.

Figure 4F:
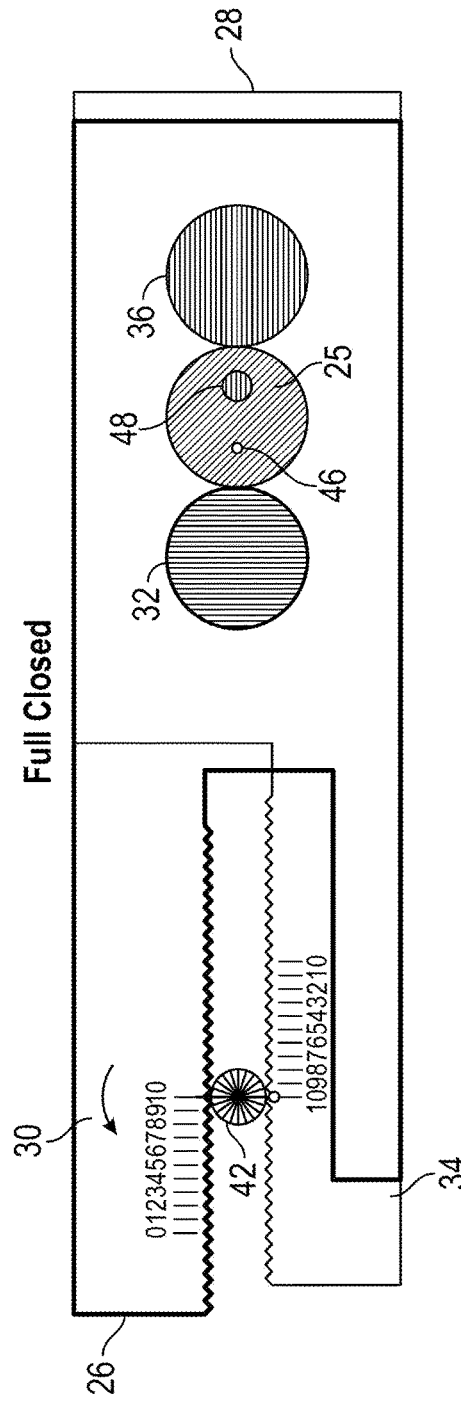

In one embodiment, reference apertures are also provided in the shutter blades. For example, FIG. 4A through FIG. 4F show the relative positions of a pinhole reference aperture 46 in the first shutter blade 26, and a larger reference aperture 48 in the second shutter blade 28. In one embodiment, the pinhole reference aperture 46 has a diameter of about 0.5 mm or less. In another embodiment, the larger reference aperture 48 has a diameter less than 25 percent of the diameter of the first and second light transmitting apertures 32 and 36. The pinhole reference aperture 46 and the large reference aperture 48 are positioned on either side of the respective first or second light transmitting aperture 26 or 28, such that they are at a maximum distance of separation in the full open position shown in FIG. 4A, and overlapping after 8 steps as shown in FIG. 4E. The pinhole reference aperture, positioned as in FIG. 4E, allows only small quantities of light into the detector 22, and can be used to monitor alignment or the light intensity transmitted by illuminator 12 for example. In FIG. 4F, no light may be transmitted and this step is noted as "FULL CLOSED." The reflective surface 25 is omitted from FIGS. 4A-4E, but is shown on first shutter blade 26 in FIG. 4F.

Figure 5A:
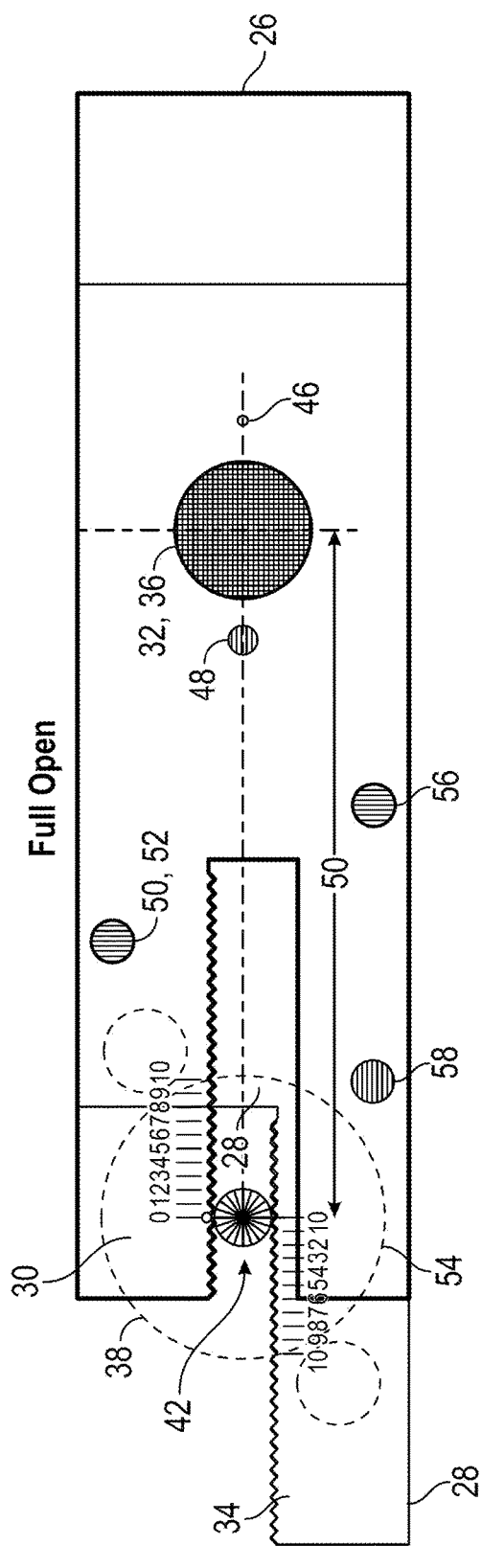
Figure 5B:
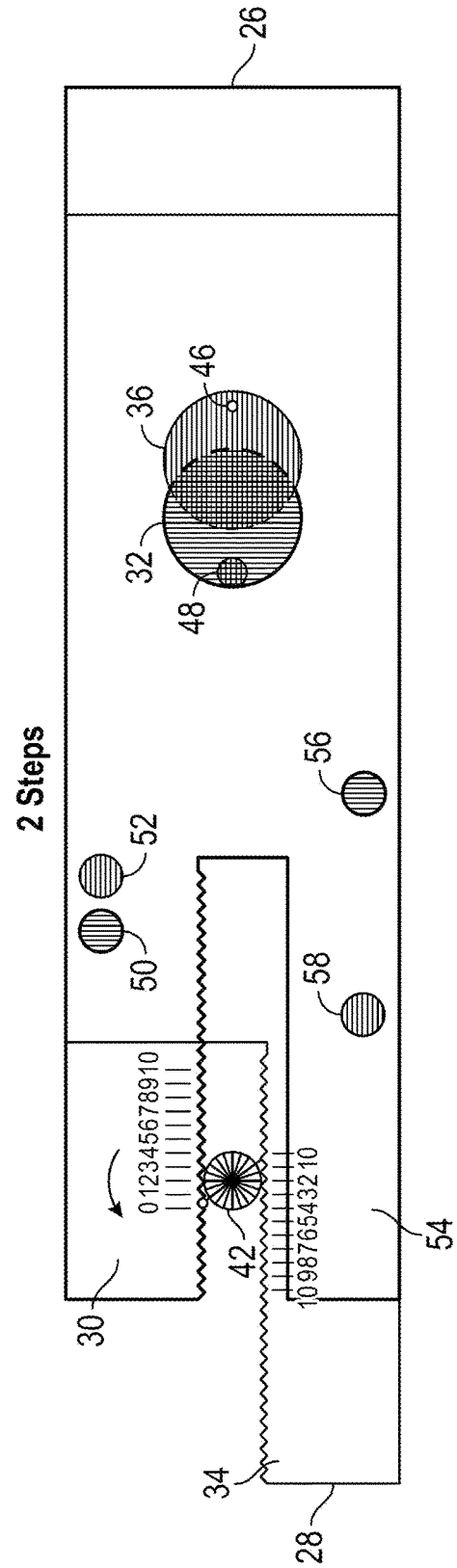
Figure 6C:
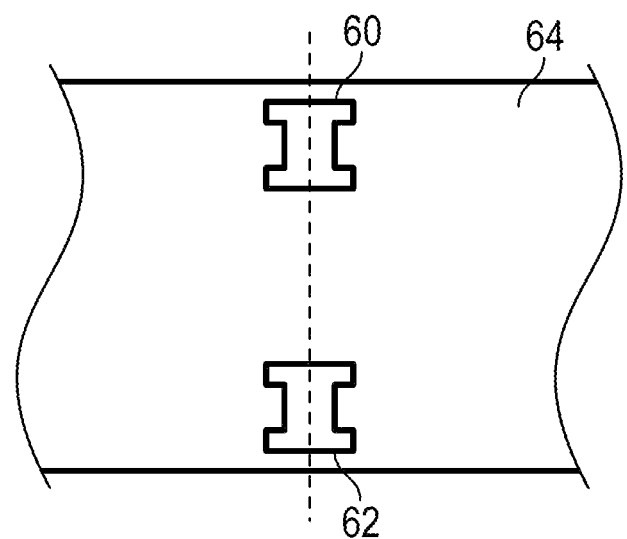

In another embodiment, and as shown schematically in FIG. 5A through 5E, a first open-biased reference aperture 50 in the first shutter blade 26 and a second open-biased reference aperture 52 in the second shutter blade 28 are positioned to completely overlap in the full open position; the full open position defined as complete overlap of first and second light transmitting apertures 32 and 36, respectively, and as shown in FIG. 5A. A first sensor 60, functionally referred to as a blades-open sensor and shown in FIGS. 6A-6C, is positioned on a back plate 64 supporting the shutter assembly 18 and aligned with the first and second open-biased reference apertures 50 and 52, respectively, in the full open position. Similarly, first closed-biased reference aperture 56 and second closed-biased reference aperture 58 are positioned to completely overlap in the full closed position as shown in FIG. 5F. A second sensor 62, functionally referred to as a blades-closed sensor and shown in FIGS. 6A-6C, is positioned on a back plate 64 supporting the shutter assembly 18 and aligned with the first and second closed-biased reference apertures 56 and 58, respectively, in the full closed position.

From the above description, it is clear that the inventive concept(s) disclosed herein is well adapted to carry out the objects and to attain the advantages mentioned herein as well as those inherent in the inventive concept disclosed herein. While exemplary embodiments of the inventive concept disclosed herein have been described for purposes of this disclosure, it will be understood that numerous changes may be made which will readily suggest themselves to those skilled in the art and which are accomplished without departing from the scope of the inventive concept disclosed herein and defined by the appended claims.

What is claimed is:

1. A shutter assembly, comprising:
    an illuminator;
    a support positioned to support a vessel containing an assay sample proximate to the illuminator;
    a shutter assembly comprising a first shutter blade, a second shutter blade, and a motor,
    the first shutter blade having a first toothed arm extending therefrom and a first light transmitting aperture therein;
    the second shutter blade positioned adjacent and parallel to the first shutter blade, the second shutter blade having a second toothed arm extending therefrom and a second light transmitting aperture therein, the first and second shutter blades supported to allow parallel linear motion; and
    a motor having a gear disposed between, and meshed with, the first and second toothed arms such that rotation of the gear causes the first and second shutter blades to move linearly in opposite directions between an open position in which the first and second light transmitting apertures are in an overlapping relationship with respect to one another along the optical axis, and a closed position in which the first and second light transmitting apertures are in a non-overlapping relationship with respect to one another, and
    wherein the shutter assembly and the assay are positioned along an optical axis extending from the illuminator, through the assay sample and the first and second light transmitting apertures of the shutter assembly when the first and second shutter blades are in the open position.

2. The shutter assembly of claim 1, wherein the motor and gear provide a direct drive mechanism.

3. The shutter assembly of claim 1, wherein the motor is a stepper motor.

4. The shutter assembly of claim 1, wherein the motor is a battery-powered stepper motor.

5. The shutter assembly of claim 1, wherein at least a portion of one of the first and second shutter blades has a polished reflective surface.

6. The shutter assembly of claim 1, further comprising a first reference aperture in the first shutter blade positioned to align with the second light transmitting aperture in the second blade prior to alignment of the first and second light transmitting apertures in the open position.

7. The shutter assembly of claim 6, wherein the first reference aperture is positioned along a center line connecting the first light transmitting aperture and the second light transmitting aperture, such that overlap of the first reference aperture with the second light transmitting aperture provides a trace of the movement of the first and second shutter blades between the closed position and the open position.

8. The shutter assembly of claim 6, wherein the reference aperture has a diameter less than 25 percent of the diameter of the first and second light transmitting apertures.

9. The shutter assembly of claim 6, wherein the reference aperture is a pinhole having a diameter of 0.5 mm or less.

10. The shutter assembly of claim 6, further comprising a second reference aperture in the second shutter blade positioned along the center line.

11. The shutter assembly of claim 1, further comprising a first open-biased reference aperture in the first shutter blade and a second open-biased reference aperture in the second shutter blade, the first and second open-biased reference apertures positioned such that they overlap only at the open position.

12. The shutter assembly of claim 11, wherein the first and second open-biased reference apertures have a diameter less than 25 percent of the diameter of the first and second light transmitting apertures.

13. The shutter assembly of claim 11, further comprising a first sensor positioned adjacent the first and second open-biased reference apertures in the overlapping position, so as to confirm that the first and second shutter blades are in the open position.

14. The shutter assembly of claim 1, further comprising a first closed-biased reference aperture in the first shutter blade and a second closed-biased reference aperture in the second shutter blade, the first and second closed-biased reference apertures positioned such that they overlap only at the closed position.

15. The shutter assembly of claim 14, wherein the first and second closed-biased reference apertures have a diameter less than 25 percent of the diameter of the first and second light transmitting apertures.

16. The shutter assembly of claim 14, further comprising a second sensor positioned adjacent the first and second open-biased reference apertures in the overlapping position, so as to confirm that the first and second shutter blades are in the open position.

17. A sample analyzer, comprising:
    an illuminator;
    a support positioned to support a sample vessel containing an assay sample proximate the illuminator, such that the illuminator causes luminescence or fluorescence of the assay sample;

a detector positioned along an optical axis extending from the illuminator, through the assay sample, to the detector, so as to detect the luminescence or fluorescence of the assay sample; and a shutter assembly positioned along the optical axis and adjacent the detector, operable to interrupt light from the illuminator, the shutter assembly having:

a first shutter blade with a first toothed arm extending therefrom and a first light transmitting aperture therein;

a second shutter blade positioned adjacent and parallel to the first shutter blade, the second shutter blade having a second toothed arm extending therefrom and a second light transmitting aperture therein, the first and second shutter blades supported to allow parallel linear motion; and a motor having a gear disposed between and meshed with the first and second toothed arms such that rotation of the gear causes the first and second shutter blades to move linearly in opposite directions between an open position in which the first and second light transmitting apertures are in an overlapping relationship with respect to one another, and a closed position in which the first and second light transmitting apertures are in a non-overlapping relationship with respect to one another wherein the assay sample is disposed in between the illuminator and the shutter assembly along the optical axis wherein the apparatus is configured with an illumination mode and a measurement mode, wherein during the illumination mode the motor moves the first and second shutter blades to the closed position and the illuminator is operated to illuminate the assay sample;

wherein during the measurement mode the illuminator is operated to discontinue illuminating the sample;

further wherein during the measurement mode the motor moves the first and second shutter blades to the open position such that luminescence from the assay sample passes through the first and second light transmitting apertures to the detector along the optical axis.

18. The sample analyzer of claim 17, wherein the detector is a photomultiplier tube.

19. The sample analyzer of claim 17, wherein the detector is positioned less than 10 mm from the assay sample.

20. The sample analyzer of claim 17, wherein the detector is positioned 5 mm to 15 mm from the illuminator.

21. The sample analyzer of claim 17, wherein a reflective surface is provided on at least a portion of the first or second shutter blades, wherein that portion represents a shutter blade surface adjacent the assay sample when the first and second light transmitting apertures are in the closed position.

22. A method of analyzing as assay sample, comprising:
obtaining a sample analyzer comprising:
an illuminator;
a support positioned to support a sample vessel containing an assay sample proximate the illuminator;
a detector positioned along an optical axis extending from the illuminator, through the assay sample, to the detector; and a shutter assembly, positioned along the optical axis and adjacent the detector, the shutter assembly comprising:

a first shutter blade having a first toothed arm extending therefrom and a first light transmitting aperture therein;

a second shutter blade positioned adjacent and parallel to the first shutter blade, the second shutter blade having a second toothed arm extending therefrom and a second light transmitting aperture therein, the first and second shutter blades supported to allow parallel linear motion; and a motor having a gear disposed between, and meshed with, the first and second toothed arms such that rotation of the gear causes the first and second shutter blades to move linearly in opposite directions between an open position in which the first and second light transmitting apertures are in an overlapping relationship with respect to one another, and a closed position in which the first and second light transmitting apertures are in a non-overlapping relationship with respect to one another wherein the assay sample is disposed in between the illuminator and the shutter assembly along the optical axis;

supporting the sample vessel containing the assay sample proximate to the illuminator;

illuminating the assay sample to cause luminescence of the assay sample during an illumination mode of the sample analyzer;

operating the shutter assembly to cause the first and second shutter blades to reach and maintain a closed position during the illumination mode;

discontinuing the illumination of the sample during a measurement mode of the sample analyzer, operating the shutter assembly to cause the first and second shutter blades to reach and maintain an open position during the measurement mode such that luminescence from the assay passes through the first and second light transmitting apertures towards the detector along the optical axis; and measuring the luminescence or fluorescence.

23. The method of claim 22, wherein the motor and gear provide a direct drive mechanism.

24. The method of claim 22, wherein the motor is a stepper motor.

25. The method of claim 22, wherein a reflective surface is provided on at least a portion of the first or second shutter blades, wherein that portion represents a shutter blade surface adjacent the assay sample when the first and second light transmitting apertures are in the closed position.

26. The method of claim 22, wherein the motor is a battery-powered stepper motor.

27. The method of claim 22, wherein the motor has a single gear disposed between, and meshed with, the first and second toothed arms.

28. The method of claim 22, wherein the shutter assembly further comprises a first reference aperture in the first shutter blade, positioned to align with the second light transmitting aperture in the second blade prior to alignment of the first and second light transmitting apertures in the open position.

* * * * *